US012788217B2

(12) United States Patent
Inoue

(10) Patent No.: US 12,788,217 B2
(45) Date of Patent: Nov. 10, 2026

(54) ENDOSCOPE WITH ELEVATOR OPERATION LEVER WITH ADJUSTABLE ROTATIONAL MOVEMENT RANGE

(71) Applicant: FUJIFILM Corporation, Tokyo (JP)

(72) Inventor: Masaya Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 336 days.

(21) Appl. No.: 18/459,437

(22) Filed: Sep. 1, 2023

(65) Prior Publication Data

US 2023/0404368 A1 Dec. 21, 2023

Related U.S. Application Data

(63) Continuation of application No. PCT/JP2022/002874, filed on Jan. 26, 2022.

(30) Foreign Application Priority Data

Mar. 3, 2021 (JP) ................................ 2021-033545

(51) Int. Cl.
*A61B 1/00* (2006.01)
*A61B 1/018* (2006.01)

(52) U.S. Cl.
CPC .......... *A61B 1/00087* (2013.01); *A61B 1/018* (2013.01)

(58) Field of Classification Search
CPC ............ A61B 1/00149; A61B 1/00098; A61B 1/00066; A61B 1/0052; A61B 1/009;
(Continued)

(56) References Cited

U.S. PATENT DOCUMENTS

2013/0190561 A1* 7/2013 Oskin .................... A61B 1/005 600/110
2016/0089004 A1 3/2016 Morimoto
(Continued)

FOREIGN PATENT DOCUMENTS

JP H05115431 5/1993
JP 2016067768 5/2016
(Continued)

OTHER PUBLICATIONS

"International Search Report (Form PCT/ISA/210) of PCT/JP2022/002874", mailed on Mar. 22, 2022, with English translation thereof, pp. 1-5.
(Continued)

*Primary Examiner* — Anhtuan T Nguyen
*Assistant Examiner* — Li-Ting Song
(74) *Attorney, Agent, or Firm* — JCIPRNET

(57) ABSTRACT

An endoscope according to the embodiment of the present invention includes a bending operating member and an elevator operation lever that displaces an elevation angle of a treatment tool elevator for elevating a treatment tool provided in a distal end of an insertion part, the bending operating member and the elevator operation lever being attached to a body part of an operating part, in which the elevator operation lever includes a finger hook part inside which a rotational movement regulating member is provided, and by bringing the rotational movement regulating member and an outer peripheral surface of the body part of the operating part into contact with each other, rotational movement of the elevator operation lever is regulated.

5 Claims, 12 Drawing Sheets

(58) Field of Classification Search
CPC ..... A61B 1/0057; A61B 1/005; A61B 1/0051; A61B 1/008; A61B 1/018; A61B 1/00087
See application file for complete search history.

(56) References Cited

U.S. PATENT DOCUMENTS

| | | | | |
|---|---|---|---|---|
| 2016/0089125 | A1 | 3/2016 | Morimoto | |
| 2019/0239739 | A1 | 8/2019 | Hiraoka | |
| 2020/0315428 | A1* | 10/2020 | Harada | A61B 1/00112 |
| 2024/0156334 | A1* | 5/2024 | Nakamura | A61B 1/0057 |
| 2024/0268634 | A1* | 8/2024 | Sumi | A61B 1/00066 |
| 2024/0423450 | A1* | 12/2024 | Wilder | A61B 1/00066 |

FOREIGN PATENT DOCUMENTS

| | | | |
|---|---|---|---|
| JP | 2016067771 | 5/2016 | |
| JP | 2018086271 | 6/2018 | |
| WO | 2018079792 | 5/2018 | |
| WO | WO-2019146329 A1 * | 8/2019 | G02B 23/2476 |

OTHER PUBLICATIONS

"Written Opinion of the International Searching Authority (Form PCT/ISA/237) of PCT/ JP2022/002874", mailed on Mar. 22, 2022, with English translation thereof, pp. 1-6.

* cited by examiner

ENDOSCOPE WITH ELEVATOR OPERATION LEVER WITH ADJUSTABLE ROTATIONAL MOVEMENT RANGE

CROSS-REFERENCE TO RELATED APPLICATIONS

This application is a Continuation of PCT International Application No. PCT/JP2022/002874 filed on 26 Jan. 2022, which claims priority under 35 U.S.C § 119(a) to Japanese Patent Application No. 2021-033545 filed on 3 Mar. 2021. The above application is hereby expressly incorporated by reference, in its entirety, into the present application.

BACKGROUND OF THE INVENTION

1. Field of the Invention

The present invention relates to an endoscope in which a rotational movement range of an elevator operation lever can be selected according to a user's preference.

2. Description of the Related Art

In an endoscope into which a treatment tool can be inserted, there is known an endoscope in which a treatment tool elevator provided in a distal end of an insertion part and an elevator operation lever of an operating part are coupled to each other, and a posture of the elevator is displaced by rotationally moving and operating the elevator operation lever, thereby changing a protruding direction of the treatment tool.

There is an endoscope in which a rotational movement mechanism interlocked to an elevator operation lever and an elevator that has a function of regulating rotational movement and regulates a rotational movement range of the elevator. For example, in JP2016-67768A (corresponding to US2016/0089125A1), a stopper unit is provided in a rotating drum coupled to an elevator operation lever to regulate a rotational movement range of an elevator. In addition, in WO2018/079792A (corresponding to US2019/0239739A1), rotational movement range of an elevator is regulated by providing a rotational movement regulating member that moves rotationally about the same shaft as the elevator.

SUMMARY OF THE INVENTION

However, in methods of JP2016-67768A and WO2018/079792A, there is a problem that the rotational movement can only be regulated in a certain range and there is a problem that the rotational movement range of the elevator cannot be easily changed according to a user's preference in a case where the user who uses the endoscope is different.

The present invention has been made in view of such circumstances, and an object of the present invention is to provide an endoscope in which a rotational movement range of an elevator operation lever can be selected according to a user's preference.

The present invention has been made to solve the problem described above, and an endoscope according to an aspect of the present invention comprises a bending operating member; and an elevator operation lever that displaces an elevation angle of a treatment tool elevator for elevating a treatment tool provided in a distal end of an insertion part, the bending operating member and the elevator operation lever being attached to a body part of an operating part, in which the elevator operation lever includes a finger hook part inside which a rotational movement regulating member is provided, and by bringing the rotational movement regulating member and an outer peripheral surface of the body part of the operating part into contact with each other, rotational movement of the elevator operation lever is regulated.

It is preferable that a range of rotational movement of the treatment tool elevator is changed in accordance with a range of the rotational movement of the elevator operation lever.

It is preferable that, by changing a position or a shape of the rotational movement regulating member, a range of rotational movement of the treatment tool elevator is changed.

It is preferable that, by changing a height in a direction perpendicular to an installation surface or a width in a direction horizontal to the installation surface of the rotational movement regulating member, a range of rotational movement of the treatment tool elevator is changed.

It is preferable that the endoscope includes a plurality of the elevator operation levers having different positions or shapes of the rotational movement regulating members, and a range of rotational movement of the treatment tool elevator is changed as the elevator operation lever is replaced.

It is preferable that in a state where the bending operating member and the elevator operation lever are attached to the body part of the operating part, the finger hook part is attachable and detachable, and, by replacing with the finger hook part in which a position or a shape of the rotational movement regulating member is different, a range of rotational movement of the treatment tool elevator is changed.

According to an aspect of the present invention, it is possible to provide the endoscope in which a rotational movement range of an elevator operation lever can be selected according to a user's preference.

DESCRIPTION OF THE PREFERRED EMBODIMENTS

First Embodiment

Figure 1:
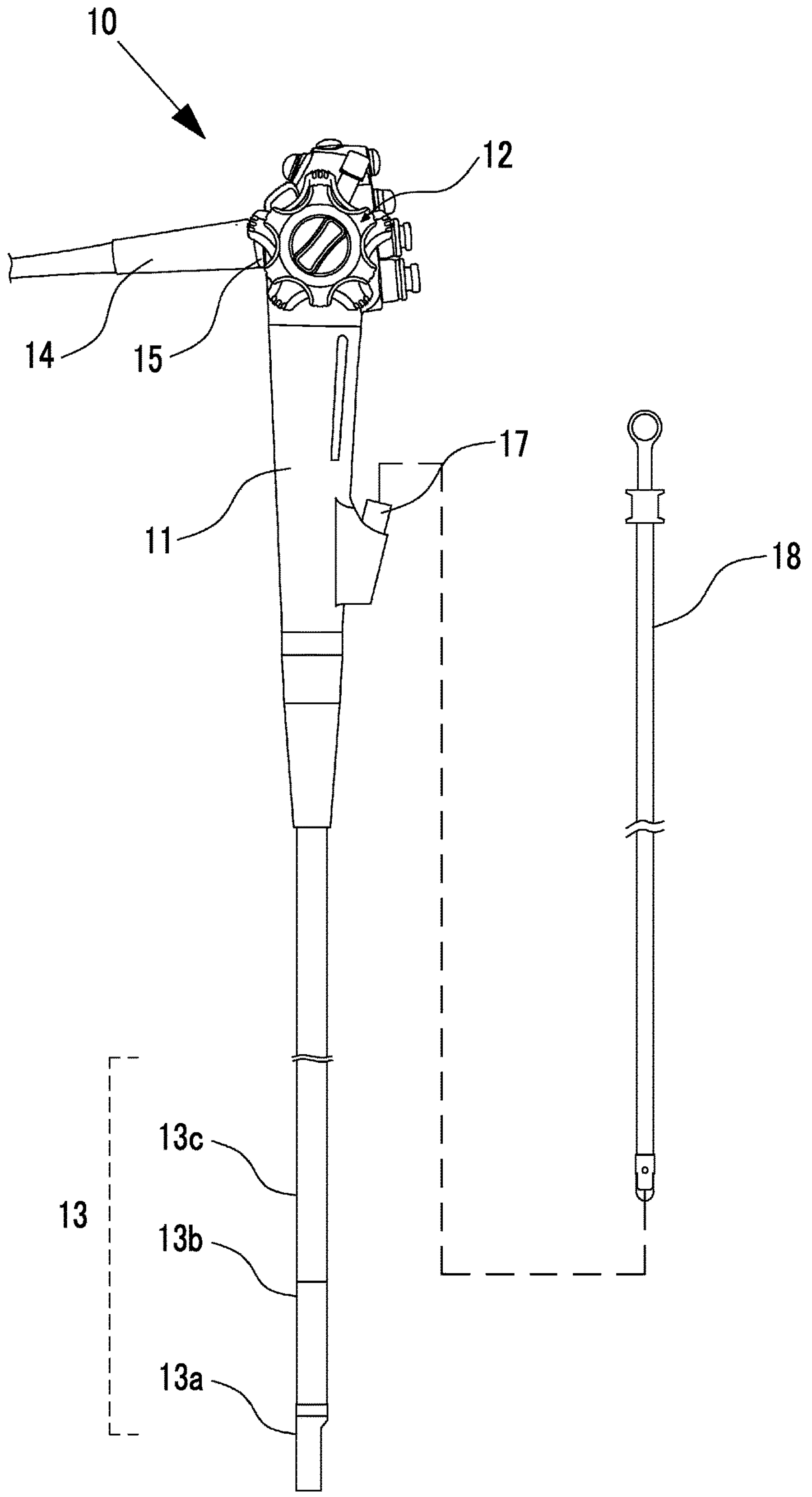
FIG. 1 is an overall view of an endoscope according to an aspect of the present invention.

As shown in FIG. 1, an endoscope 10 has a gripped part 11 gripped by a user, an operating part 12 for performing various operations, an insertion part 13 inserted into a subject, and a universal cord 14 connected to a connecting part 15. An illumination device (not shown) that supplies illumination light to the endoscope 10 and a processor device (not shown) that executes various kinds of processing according to an operation of the operating part 12 are connected to the endoscope 10 via the universal cord 14. In the insertion part 13, a distal end 13*a*, a bendable part 13*b*, and a flexible part 13*c* are coupled in this order from the distal end side toward the proximal end side.

The endoscope 10 is, for example, a side-view endoscope such as a duodenoscope, and is provided with a treatment tool insertion port 17 into which a treatment tool 18 used in a case of performing a medical treatment such as a therapy or an examination is inserted. The treatment tool 18 that is inserted passes through an insertion path disposed inside the insertion part 13 from the treatment tool insertion port 17 to the distal end 13*a*, protrudes from the distal end 13*a*, and is used for various medical treatments.

Figure 2:
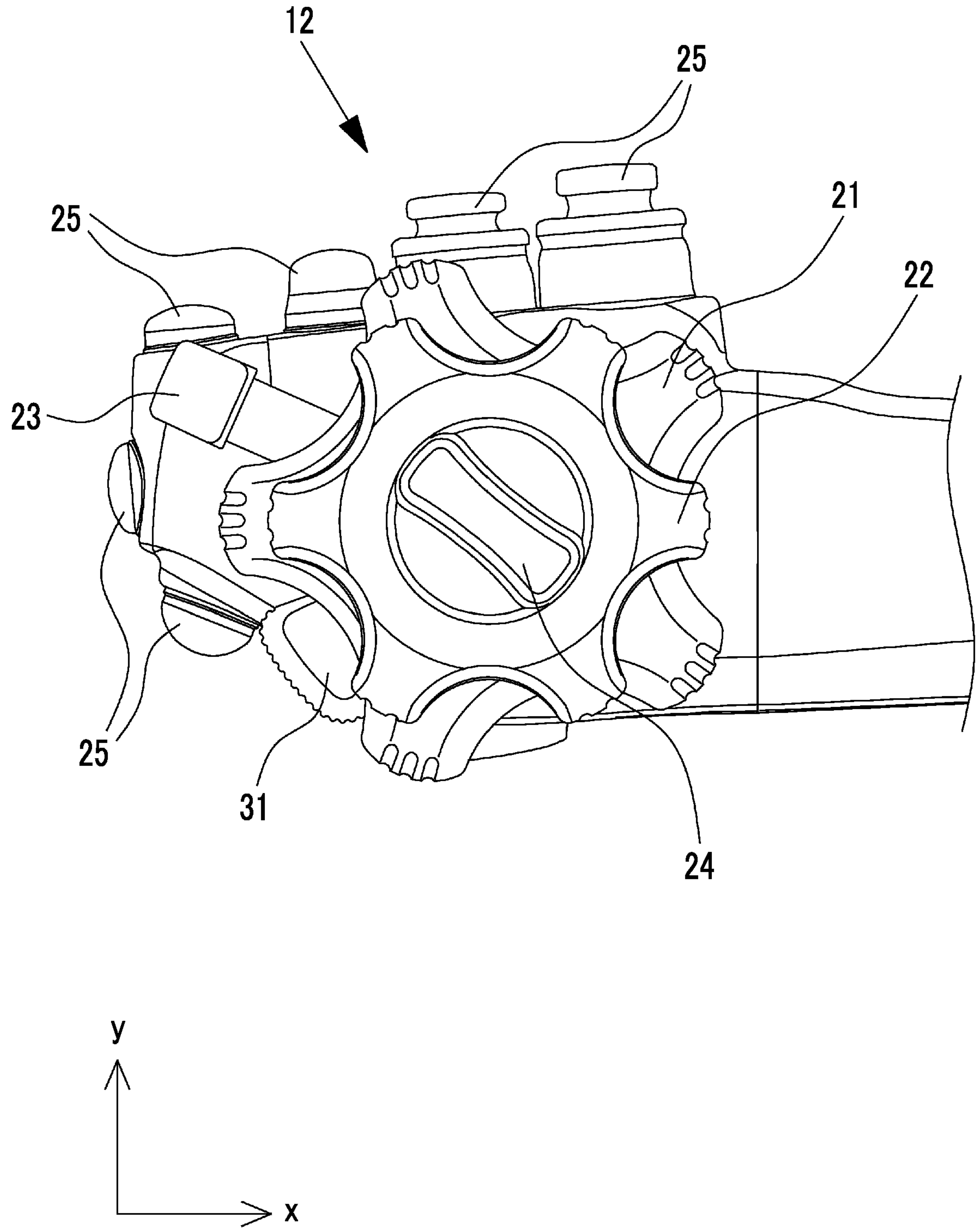
FIG. 2 is an enlarged plan view of an operating part of the endoscope.

As shown in FIG. 2, the operating part 12 has, as bending operating members, an up-down angle knob 21 that bends the bendable part 13*b* in an up-down direction, a right-left angle knob 22 that bends the bendable part 13*b* in a right-left direction, and an up-down lock lever 23 and a right-left lock handle 24 that locks or unlocks rotational movement of an angle knob by being rotationally moved and operated. By rotationally moving and operating the up-down and right-left angle knobs, the bendable part 13*b* bends and the distal end 13*a* is directed to a desired direction. In order to maintain a bent state of the bendable part 13*b*, the up-down lock lever 23 and the right-left lock handle 24 are appropriately rotationally moved and operated. Note that an outer peripheral surface 41*a* of a body part 41 of the operating part 12 is provided with a plurality of operation buttons 25 for executing various kinds of processing of the endoscope in cooperation with the processor device. In FIG. 2, a direction indicated by an arrow x is a longitudinal direction of the operating part 12, and a direction indicated by an arrow y is a width direction of the operating part 12. That is, the longitudinal direction is a direction that is vertical in a case where a user normally grips the endoscope 10, and the width direction is a direction that is perpendicular to the longitudinal direction. In addition, in the present specification, unless otherwise specified, "upward" refers to a direction toward the bending operating members from the body part 41 (from a back side to a front side in FIG. 2), and a direction opposite thereto is referred to as "downward".

Figure 3:
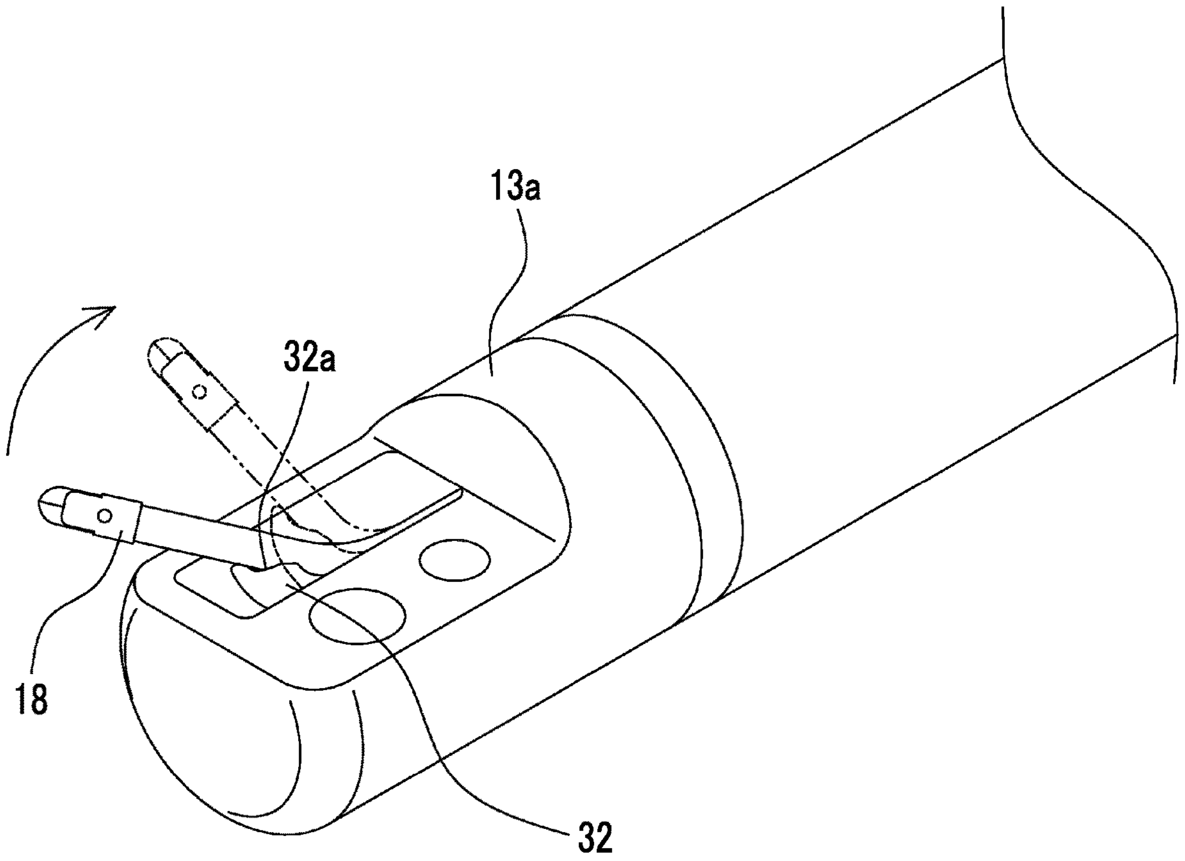
FIG. 3 is a perspective view describing a rotational movement range of an elevator.

In addition, the operating part 12 is provided with an elevator operation lever 31. The elevator operation lever 31 is connected to a treatment tool elevator 32 (hereinafter, simply referred to as an elevator) provided in the distal end 13*a* shown in FIG. 3 by a pulling wire 47 (refer to FIG. 4) inserted into the endoscope 10, and the elevator 32 is changed from a lowered posture to an elevated posture or from the elevated posture to the lowered posture by an elevator rotational movement mechanism 40 that will be described later by rotationally moving the elevator operation lever 31. In a case of performing various medical treatments, the treatment tool 18 protrudes from the distal end 13*a* along a guide surface 32*a* of the elevator 32, and a protruding direction changes in accordance with a change in the posture of the elevator 32.

Figure 4:
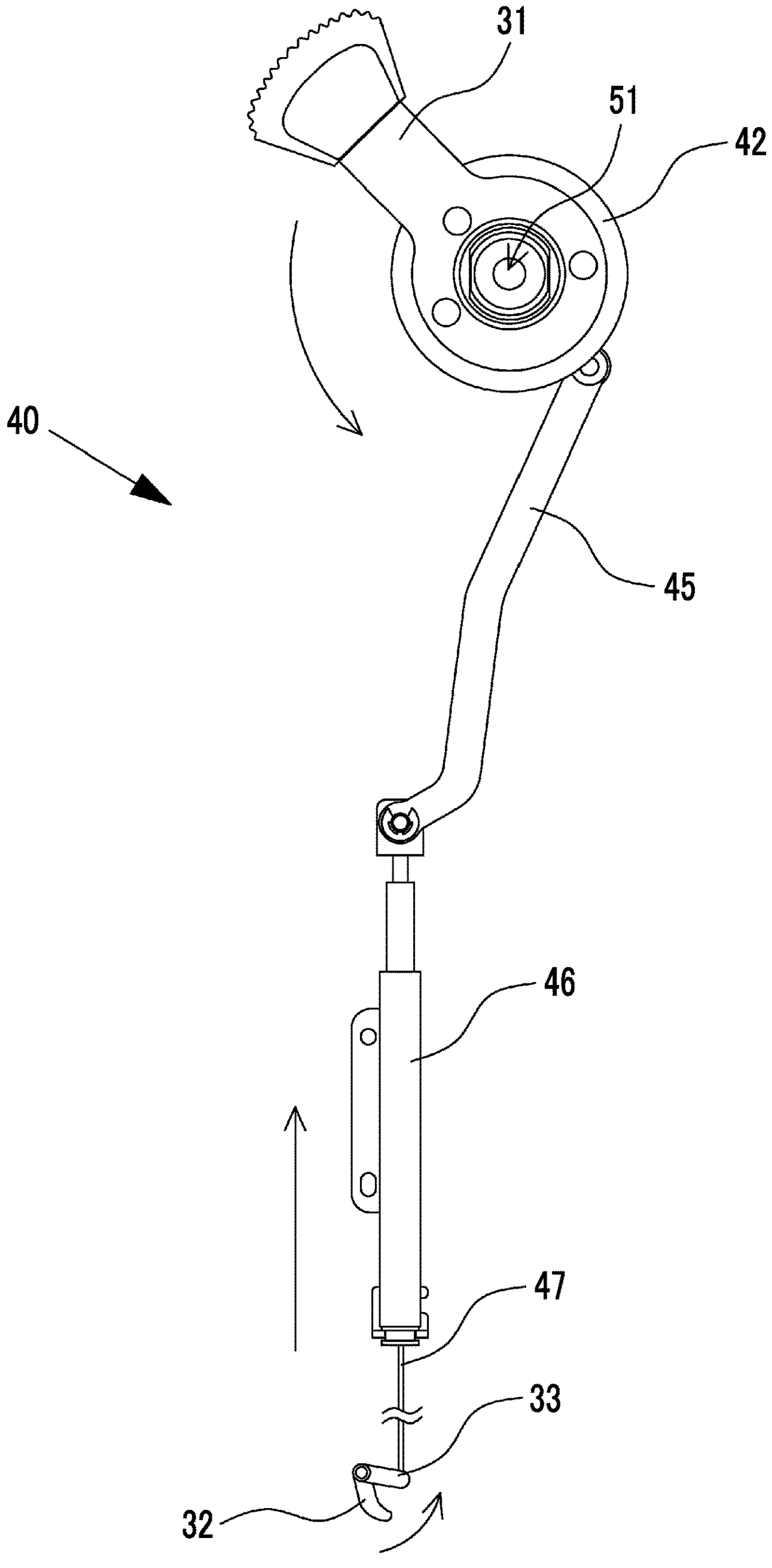
FIG. 4 is a schematic view describing an elevator rotational movement mechanism.

FIG. 4 is a schematic view describing the elevator rotational movement mechanism 40. The elevator rotational movement mechanism 40 has a rotational movement member 42, a crank member 45 coupled to the rotational movement member 42, and a slider 46 coupled to the crank member 45. The slider 46 is connected to an elevator rotational movement lever 33 for rotationally moving the elevator 32 by the pulling wire 47. The crank member 45 is a member that converts a rotational motion of the rotational movement member 42 into a linear motion of the slider 46. In addition, the elevator operation lever 31 is coupled such that an angle of the elevator 32 changes in a case where the elevator operation lever 31 moves rotationally. Accordingly, in a state where the elevator operation lever 31 is coupled to the rotational movement member 42, by rotationally moving and operating the elevator operation lever 31, the pulling wire 47 connected to the rotational movement member 42 is pushed and pulled, and the posture of the elevator 32 changes with the rotational movement of the elevator operation lever 31. For example, as shown in FIG. 4, in a case where the elevator operation lever 31 is rotationally moved in a left rotation direction (rotational movement direction R) as indicated by an arrow, the pulling wire 47 is pulled, and the elevator 32 moves rotationally in an elevated posture direction. A rotational movement range of the elevator operation lever 31 and a rotational movement range of the elevator 32 correspond to each other, and the rotational movement ranges of the elevator operation lever 31 and the elevator 32 are configured such that the rotational movement is performed within a predetermined rotational movement range using known technology. In the elevator rotational movement mechanism 40, the elevator rotational movement lever 33 may be omitted, and the pulling wire 47 and the elevator 32 may be directly connected to each other.

Figure 5:
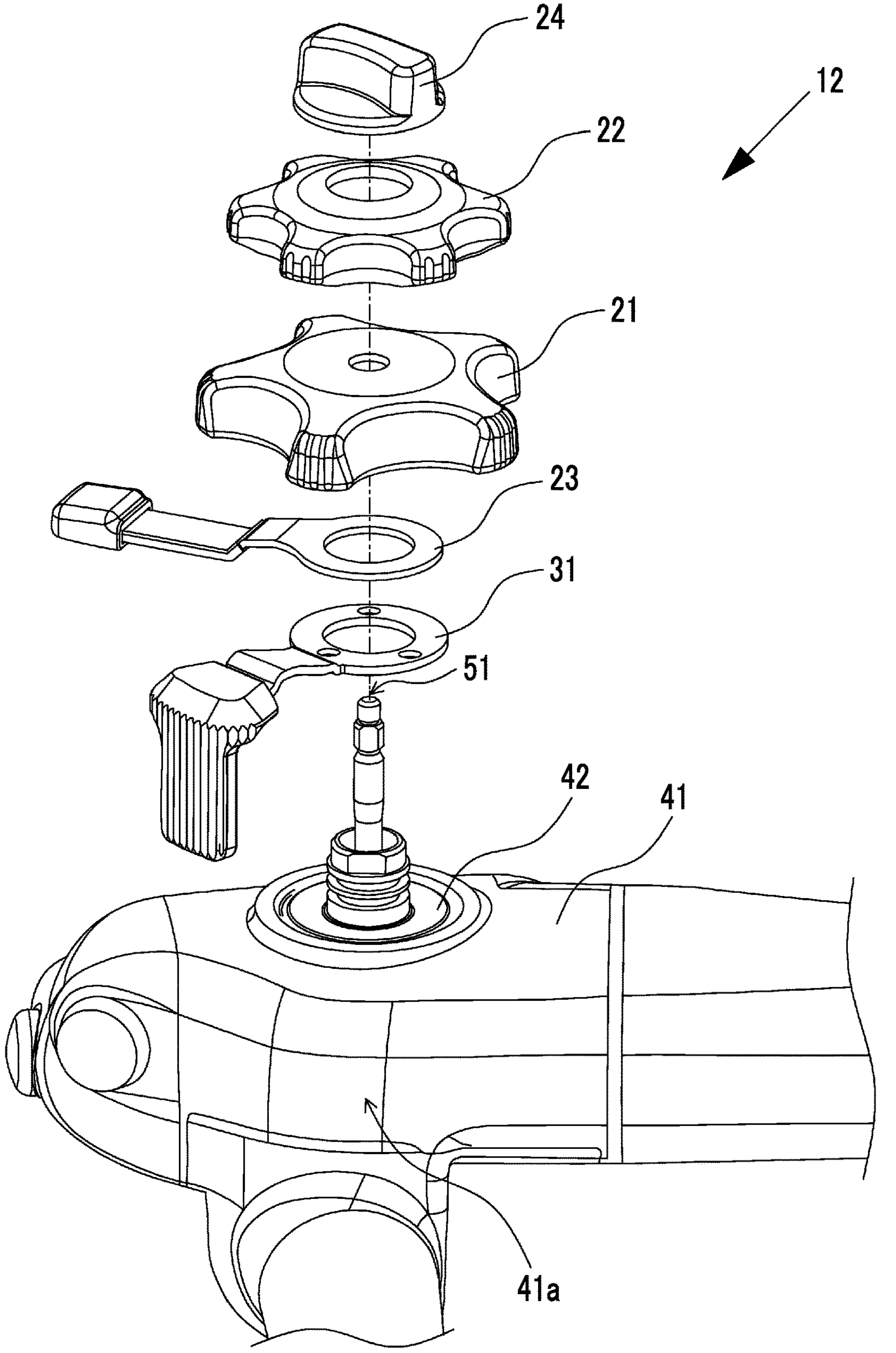
FIG. 5 is an exploded view describing an operating member attached to the operating part of the endoscope.

As shown in FIG. 5, the respective bending operating members and the elevator operation lever 31 are attached to the body part 41 of the operating part 12 such that the right-left lock handle 24, the right-left angle knob 22, the up-down angle knob 21, the up-down lock lever 23, and the elevator operation lever 31 are stacked in this order from an outside with respect to the same rotational movement shaft 51. In a case of attachment, the elevator operation lever 31 is first attached to the rotational movement shaft 51, and then the up-down lock lever 23, the up-down angle knob 21, the right-left angle knob 22, and the right-left lock handle 24 are attached to the rotational movement shaft 51 in this order such that attachment portions (not shown) provided in a center of the respective bending operating members and the elevator operation lever 31 are put to the rotational movement shaft 51. In a case where the members are attached to the body part 41, the members move rotationally independently of each other. The bending operating members and the elevator operation lever 31 are preferably attachable to and detachable from the body part 41.

Figure 6:
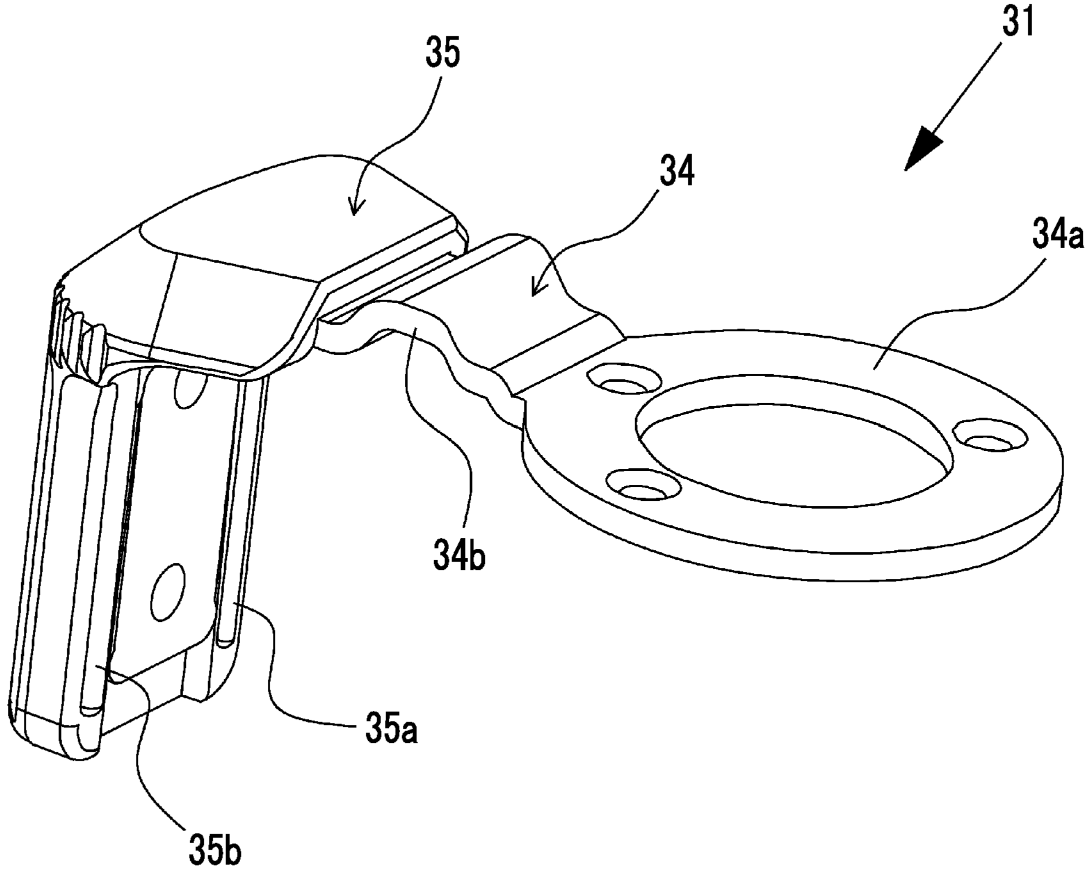
FIG. 6 is a perspective view describing an elevator operation lever.

As shown in FIG. 6, the elevator operation lever 31 is configured of an attachment member 34 formed of an annular coupling part 34*a* and an L-shaped arm part 34*b* (refer to FIG. 12) connected to the coupling part 34*a*, and a finger hook part 35. The finger hook part 35 is fixed to the arm part 34*b* by a screw (not shown) or the like with respect to the attachment member 34. In addition, rotational movement regulating members 35*a* and 35*b* are provided on both sides in a width direction inside the finger hook part 35. In a case where the elevator operation lever 31 is attached to the body part 41, and the elevator operation lever 31 is rotationally moved and operated, in a rotational movement start end side or a rotational movement terminal end side (refer to FIG. 7), the rotational movement regulating member 35*a* comes into contact with the outer peripheral surface 41*a* (refer to FIG. 5) of the body part 41 and regulates the rotational movement range of the elevator operation lever 31.

Figure 7:
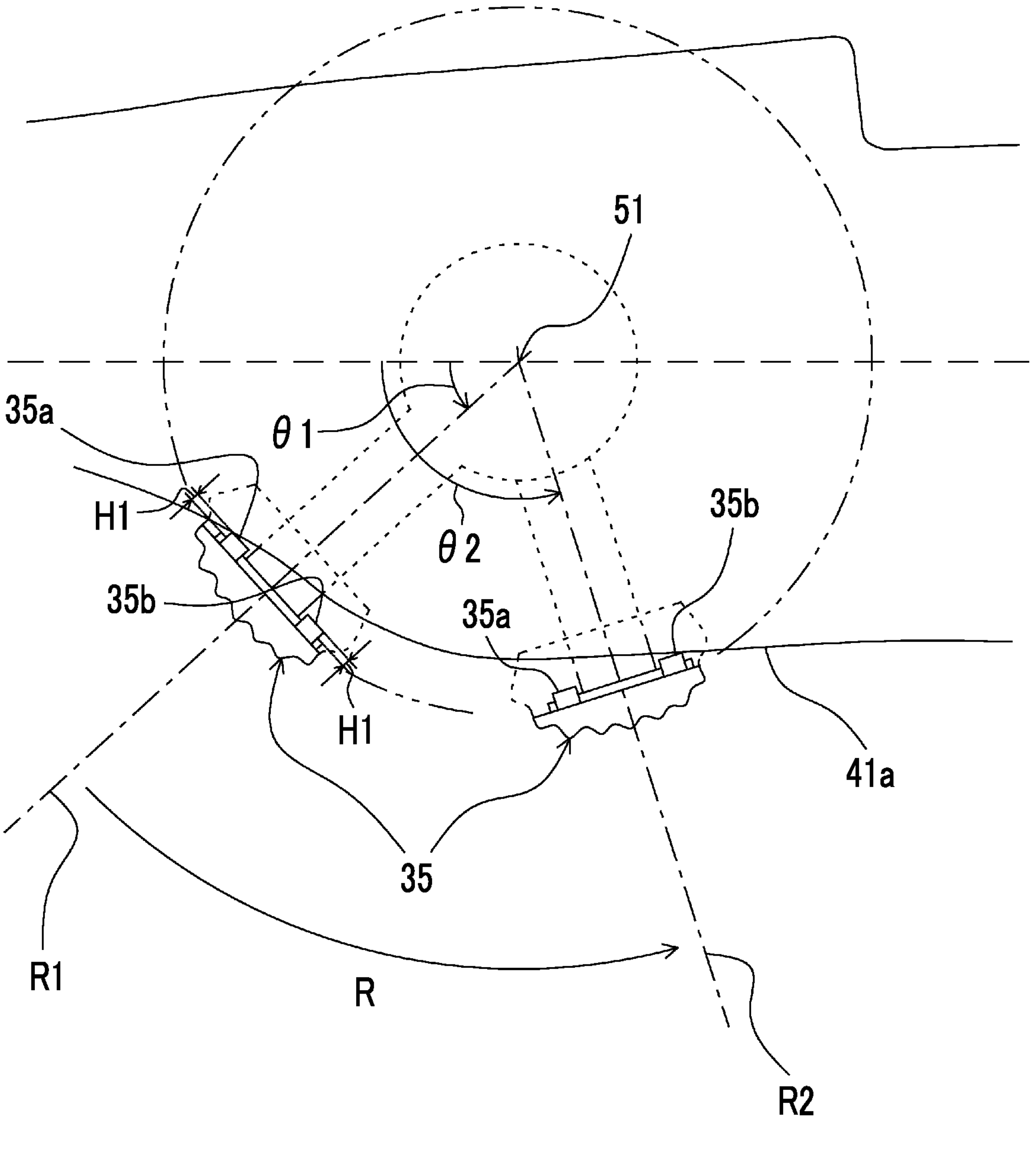
FIG. 7 is a schematic view describing a rotational movement range of the elevator operation lever.

FIG. 7 is a schematic view describing the rotational movement range of the elevator operation lever 31 having the rotational movement regulating members 35*a* and 35*b* of a height H1. In a case of rotationally moving the elevator operation lever 31 along the outer peripheral surface 41*a* of the body part 41, the finger hook part 35 seemingly appears to move rotationally along the outer peripheral surface 41*a* of the body part 41. Heights of rotational movement regulating members 35*a* and 35*b* are dimensions in a direction perpendicular to installation surfaces in a case where rotational movement regulating members 35*a* and 35*b* are provided on the finger hook part 35. The elevator operation lever 31 moves rotationally about the rotational movement shaft 51 along a direction of an arrow R. An angle between a straight line indicated by a broken line passing through the rotational movement shaft 51 along the longitudinal direction and a center line of the elevator operation lever 31 indicated by a one-dot chain line is θ and the angle θ will be described with an appropriate suffix.

As shown in FIG. 7, in a case of rotationally moving and operating the elevator operation lever 31 attached to the body part 41, in a case where the elevator operation lever 31 is in a rotational movement start end position R1 of the rotational movement start end side, the rotational movement regulating member 35*a* provided in the rotational movement start end side with respect to the body part 41 comes into contact with the outer peripheral surface 41*a* of the body part 41, and in a case where the elevator operation lever 31 is in a rotational movement terminal end position R2 of the rotational movement terminal end side, the rotational movement regulating member 35*b* provided in the rotational movement terminal end side with respect to the body part 41 comes into contact with the outer peripheral surface 41*a* of the body part 41. That is, in a case where an angle θ of a case where the rotational movement regulating member comes into contact with the outer peripheral surface 41*a* at the rotational movement start end side of the body part 41 is θ1 and an angle θ of a case where the rotational movement regulating member 35*a* comes into contact with the outer peripheral surface 41*a* at the rotational movement terminal end side is θ2, the elevator operation lever 31 moves rotationally within a range from the angle θ1 to the angle θ2.

In a case where the rotational movement range of the elevator operation lever 31 is regulated, the rotational movement range of the elevator 32 is also regulated. As shown in FIGS. 2 and 7, in a case where the elevator operation lever 31 is at the rotational movement start end position R1 that is at the angle θ1, the posture of the elevator 32 is the lowered posture in which the elevator operation lever 31 is most lowered at an angle θ1*a* that is a minimum angle θ, and, in a case where the elevator operation lever 31 is at the rotational movement terminal end position R2 that is at the angle θ2, the posture of the elevator 32 is the elevated posture in which the elevator operation lever 31 is most elevated at an angle θ2*a* that is a maximum angle θ.

Figure 8:
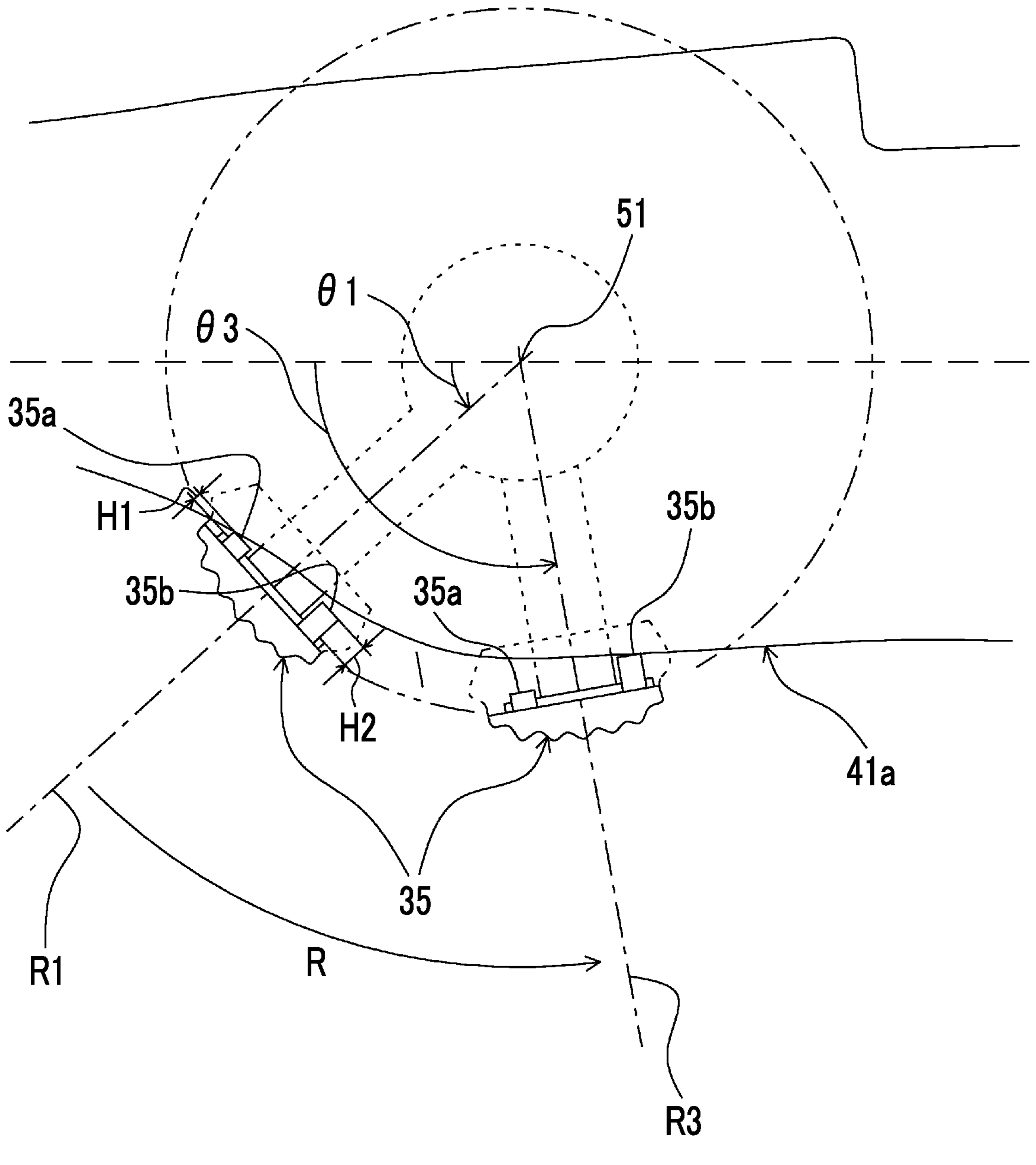
FIG. 8 is a schematic view describing a rotational movement range of an elevator operation lever in a case where a height of a rotational movement regulating member is changed.

The endoscope 10 comprises a plurality of elevator operation levers 31 having different positions or shapes of rotational movement regulating members 35*a* and 35*b*, a rotational movement range of an elevator operation lever 31 can be easily regulated as the elevator operation lever 31 is replaced with another elevator operation lever 31, and the rotational movement range of the elevator 32 can be selected according to a user's preference or content of a medical treatment. As shown in FIG. 8, in a rotational movement regulating member 35*b* at a rotational movement terminal end side of a finger hook part 35 of an elevator operation lever 31, a height H2 along a direction facing the body part 41 is formed higher compared to the rotational movement regulating member 35*b* (height H1) of FIG. 7. Accordingly, since the elevator operation lever 31 of FIG. 8 comes into contact at a rotational movement terminal end position R3 at which the angle θ is an angle θ3 smaller than the angle θ2 at the rotational movement terminal end side of a case where the elevator operation lever 31 of FIG. 7 is attached, the elevator operation lever 31 of FIG. 8 has a rotational movement range narrower than the rotational movement range of the elevator operation lever 31 of FIG. 7. Different shapes of the rotational movement regulating members 35*a* and 35*b* mean that not only heights are different as described above but also widths are different, and that shapes of the rotational movement regulating members 35*a* and 35*b* viewed from a cross-sectional direction are not circular shapes but are different shapes such as triangular shapes or quadrangular shapes. That is, in a case of replacing an elevator operation lever 31 with another elevator operation lever 31, contact surfaces of rotational movement regulating members 35*a* and 35*b* of a finger hook part 35 that come into contact with the outer peripheral surface 41*a* of the body part 41 need only to be different from each other with respect to a rotational movement direction. Widths of rotational movement regulating members 35*a* and 35*b* are dimensions in a direction horizontal to installation surfaces in a case where rotational movement regulating members 35*a* and 35*b* are provided on the finger hook part 35.

Figure 9:
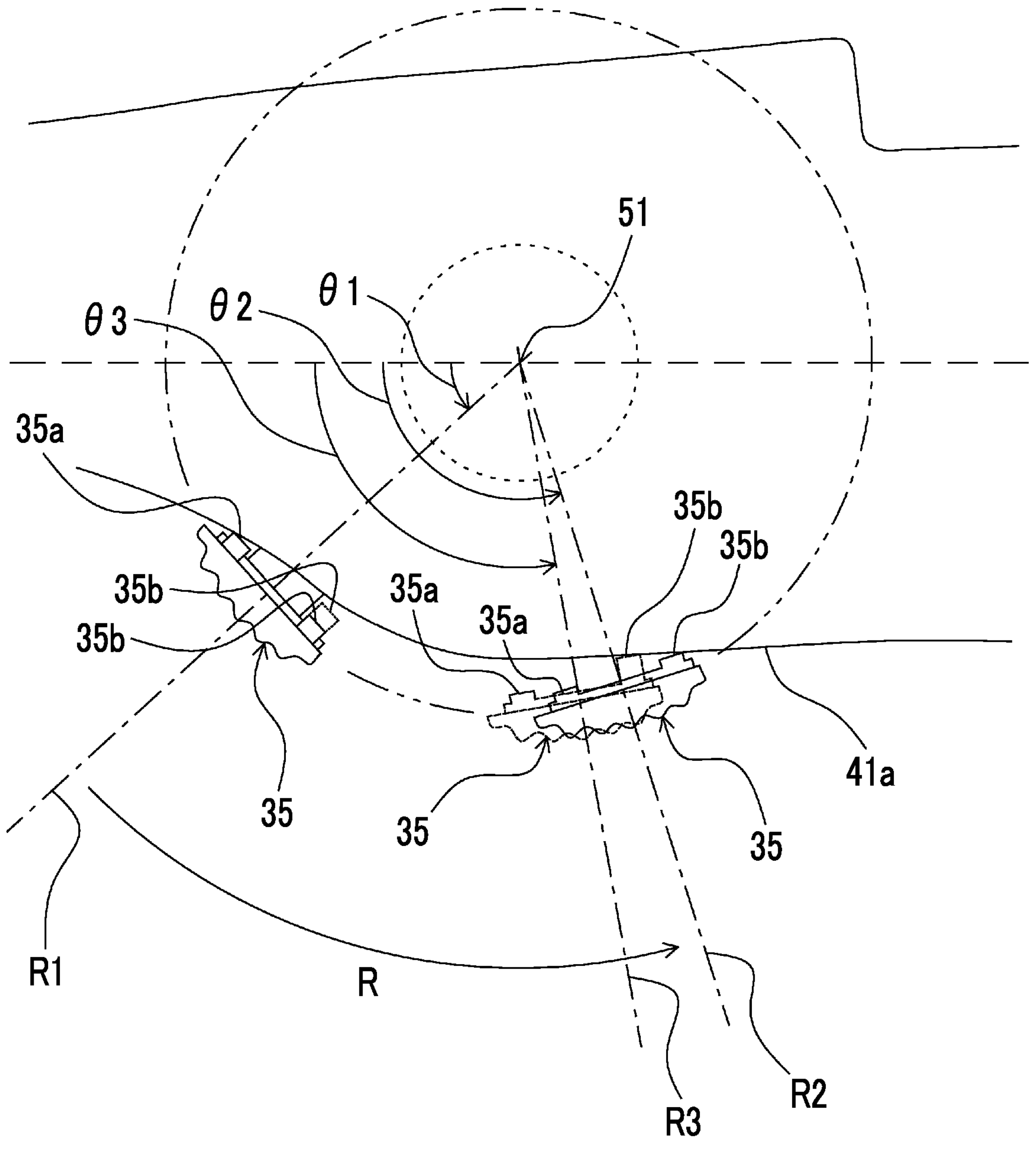
FIG. 9 is a schematic view comparing the rotational movement ranges of the elevator operation levers having different rotational movement ranges.

FIG. 9 is an explanatory view comparing the rotational movement range of the elevator operation lever 31 of FIG. 7 with the rotational movement range of the elevator operation lever 31 of FIG. 8. It can be seen that, in the elevator operation lever 31 of FIG. 7, the rotational movement is performed in a range where the angle θ is the angle θ1 to the angle θ2, the rotational movement range of the elevator operation lever 31 of FIG. 8 is narrower than the rotational movement range of FIG. 7, and the rotational movement is performed in a range where the angle θ is the angle θ1 to the angle θ3.

Figure 10:
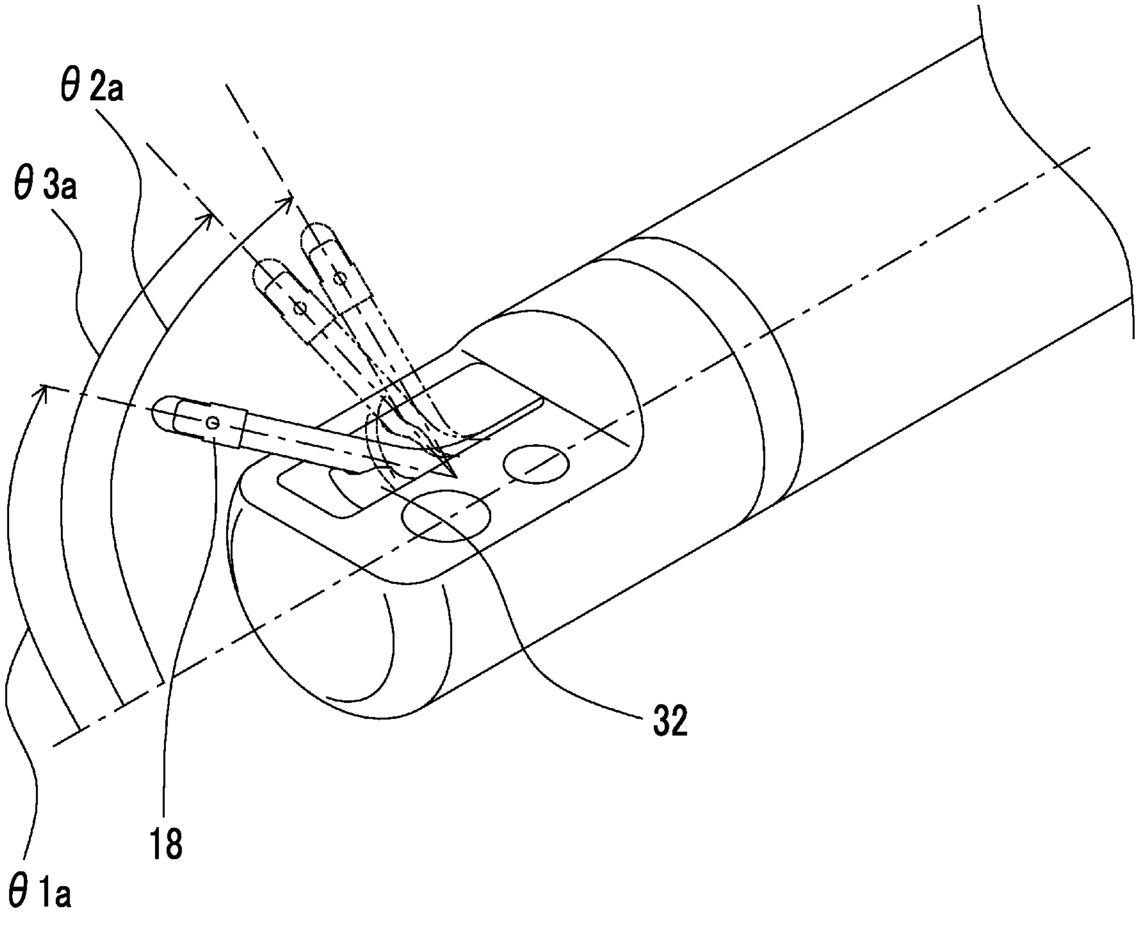
FIG. 10 is an explanatory view comparing a plurality of different rotational movement ranges in the elevator in a case where the elevator operation levers having the different rotational movement ranges are used.

That is, in a case where an elevator operation lever 31 is replaced with another elevator operation lever 31 having a rotational movement regulating member 35*a* in a different shape, rotational movement range of the elevator operation lever 31 is changed, and accordingly, the rotational movement range of the elevator 32 is also regulated. FIG. 10 shows a difference in the rotational movement ranges of the elevator 32 between the elevator operation lever 31 of FIG. 7 and the elevator operation lever 31 of FIG. 8. Referring to FIG. 2, in a case of rotationally moving the elevator operation lever 31 from left to right in FIG. 2, since the elevator 32 moves rotationally in an elevating direction, the maximum angle θ is shallower (θ3*a*<θ2*a*) and the rotational movement range is set to narrow in a case of using the elevator operation lever 31 of FIG. 8 than in a case of using the elevator operation lever 31 of FIG. 7. As described above, a user can select the rotational movement range of the elevator 32 of the elevator operation lever 31 according to a preference and content of a medical treatment.

Second Embodiment

Figure 11:
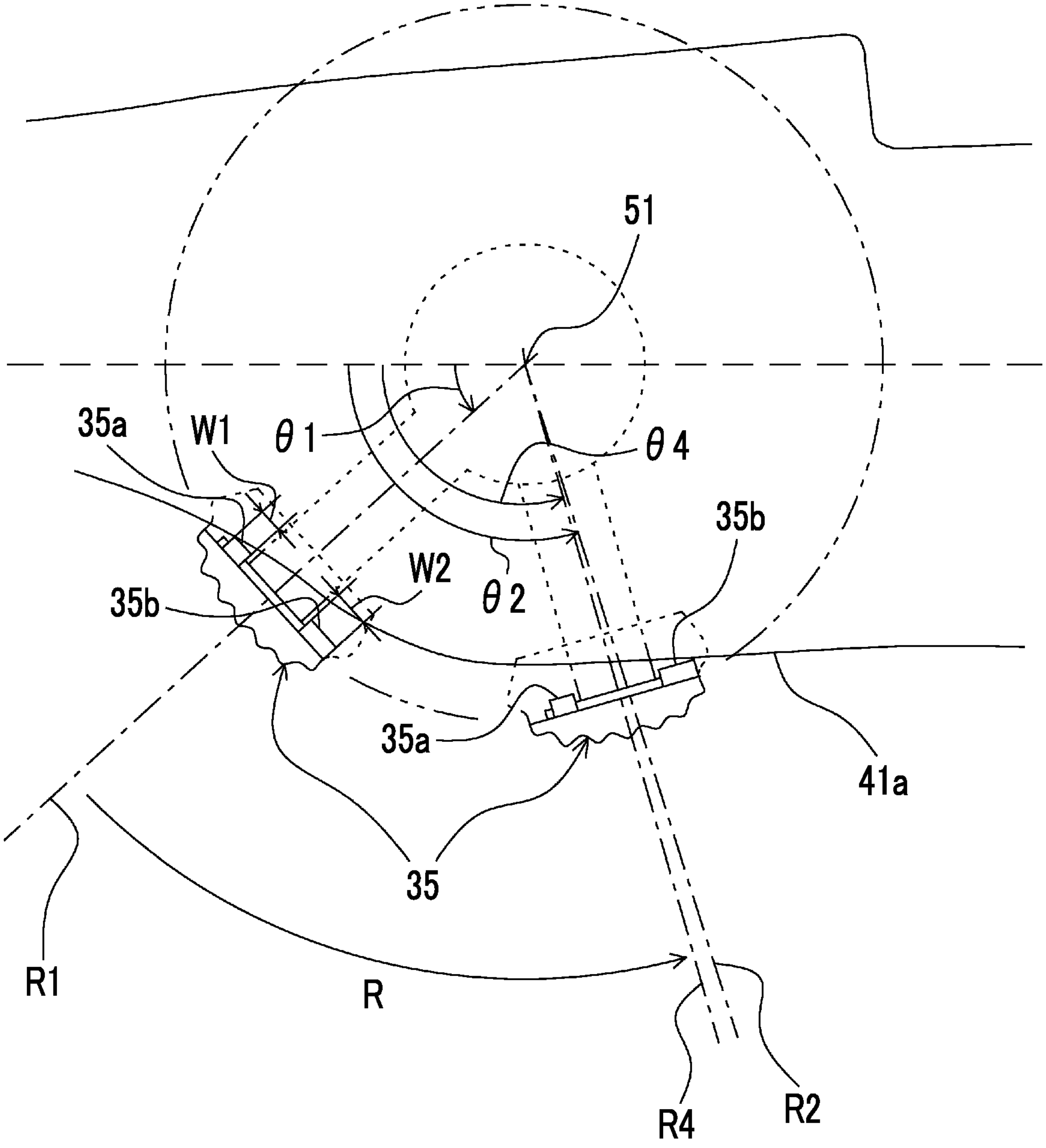
FIG. 11 is a schematic view describing the rotational movement range of the elevator operation lever in a case where a width of the rotational movement regulating member is changed.

In the elevator operation lever 31 of the first embodiment, heights of rotational movement regulating members 35*a* and 35*b* are changed, but widths of rotational movement regulating members 35*a* and 35*b* may be changed. As shown in FIG. 11, a rotational movement regulating member 35*a* at the rotational movement start end side has a width W1, but a rotational movement regulating member 35*b* at the rotational movement terminal end side has a width W2 longer than the width W1. Therefore, a rotational movement terminal end position R4 of an elevator operation lever 31 in FIG. 11 is closer to a front side with respect to the rotational movement direction R than the rotational movement terminal end position R2 of the elevator operation lever 31 in FIG. 7. In addition, the elevator operation lever 31 in this case moves rotationally within a range from the angle θ1 to an angle θ4. As described above, a rotational movement range of an elevator operation lever 31 can also be regulated by changing a width instead of changing a height of a rotational movement regulating member 35*a* or 35*b*.

Third Embodiment

Figure 12:
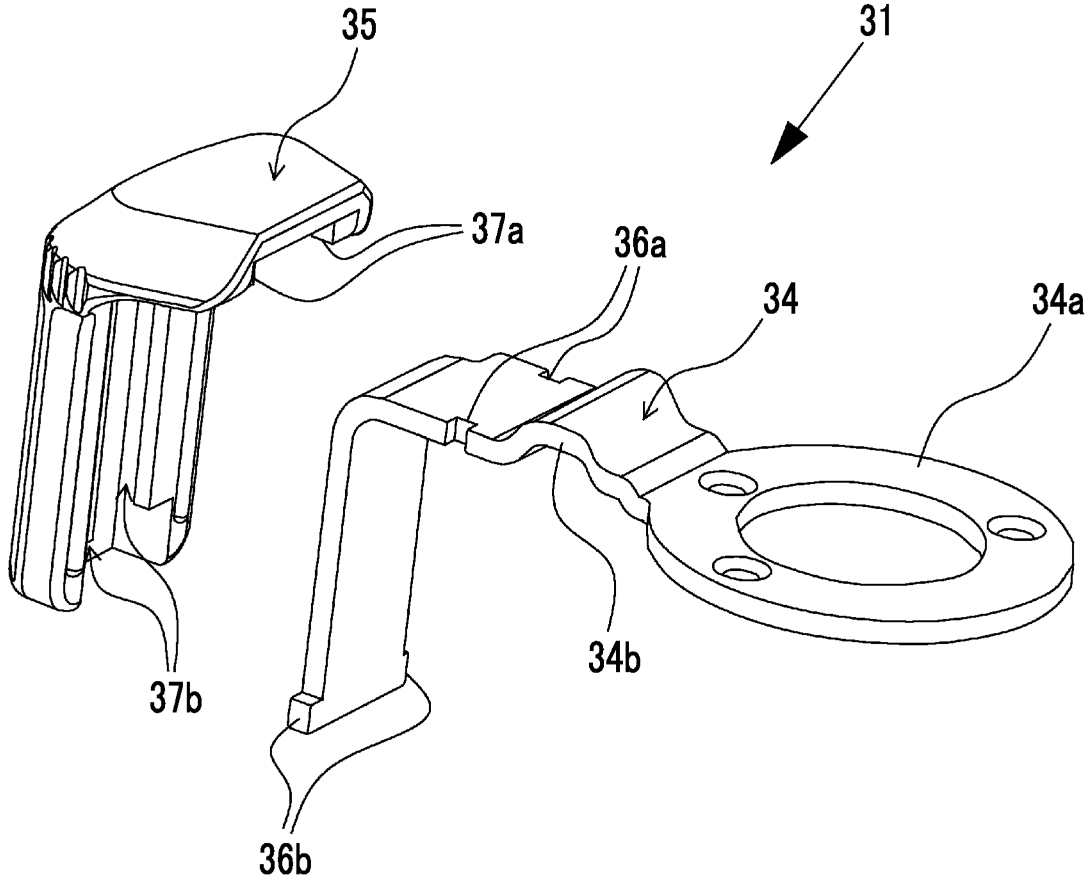
FIG. 12 is an explanatory view of the elevator operation lever in which a finger hook part is attachable and detachable.

In the elevator operation levers 31 of the first embodiment and the second embodiment, the attachment member 34 and the finger hook part 35 are fixed to each other with a screw or the like, and in a case of replacing the elevator operation lever 31, the bending operating member such as the up-down angle knob 21 attached upward above the elevator operation lever 31 need to be removed. However, in an elevator operation lever 31 of the third embodiment, as shown in FIG. 12, a finger hook part 35 is attachable to and detachable from an attachment member 34. In the elevator operation lever 31 of the present embodiment, the attachment member 34 is provided with a fitting groove portion 36*a* and a fitting projection portion 36*b* formed in a T shape. On the other hand, the finger hook part 35 is provided with a fitting protrusion portion 37*a* to be fitted to the fitting groove portion 36*a* and a fitting recess portion 37*b* to be fitted to the fitting projection portion 36*b*. In a case of attaching the finger hook part 35 to the attachment member 34, first, the finger hook part 35 is put inward in a radial direction so as to cover the attachment member 34, and is further pushed downward (in a direction bent in an L shape) to be externally fitted. Although the finger hook part 35 is not completely fixed like being fixed by a screw, since the elevator operation lever 31 is normally pressed downward in a case of being rotationally moved and operated, no inconvenience occurs in a case where the finger hook part 35 is fixed to the attachment member 34 with respect to a circumferential direction and the radial direction in which the elevator operation lever 31 moves rotationally. With such a configuration, the finger hook part 35 of the elevator operation lever 31 can be replaced without removing the bending operating member, and a user can easily replace the elevator operation lever 31 with an elevator operation lever 31 having a desired rotational movement range.

In each of the embodiments described above, an example in which the finger hook part 35 has a pair of rotational movement regulating members 35*a* and 35*b* on both sides of an inner side surface of the finger hook part 35 has been described, but only one side may be provided with a rotational movement regulating member. That is, in a case where only a rotational movement regulating member 35*a* serving as the rotational movement start end side of an elevator operation lever 31 is provided, rotational movement at the start end side can be regulated, and in a case where only a rotational movement regulating member 35*b* serving as the rotational movement terminal end side is provided, rotational movement at the rotational movement terminal end side can be regulated. In addition, in FIG. 8, only the rotational movement regulating member 35*b* on the rotational movement terminal end side is changed, but only a rotational movement regulating member 35*a* on the rotational movement start end side may be changed, and shapes and arrangements of a rotational movement regulating member 35*a* and a rotational movement regulating member 35*b* can be appropriately modified. As described above, by regulating rotational movement of an elevator operation lever 31 in any direction or by determining shapes and arrangements of rotational movement regulating members 35*a* and 35*b* in accordance with a purpose and comprising a plurality of elevator operation levers 31, a user can select and use an elevator operation lever 31 that is most appropriate for a medical treatment.

EXPLANATION OF REFERENCES

10: endoscope
11: gripped part
12: operating part
13: insertion part
13*a*: distal end
13*b*: bendable part
13*c*: flexible part
14: universal cord
15: connecting part
17: treatment tool insertion port
18: treatment tool
21: up-down angle knob
22: right-left angle knob
23: up-down lock lever
24: right-left lock handle
25: operation button
31: elevator operation lever
32: treatment tool elevator (elevator)
32*a*: guide surface
33: elevator rotational movement lever
34: attachment member
34*a*: coupling part
34*b*: arm part
35: finger hook part
35*b*: rotational movement regulating member
36*a*: fitting groove portion
36*b*: fitting projection portion
37*a*: fitting protrusion portion
37*b*: fitting recess portion
40: elevator rotational movement mechanism
41: body part
41*a*: outer peripheral surface
42: rotational movement member
45: crank member
46: slider
47: pulling wire
51: rotational movement shaft
θ, θ1, θ2, θ3, θ4: angle
θ1*a*, θ2*a*, θ3*a*: angle
R: rotational movement direction
R1: rotational movement start end position
R2, R3, R4: rotational movement terminal end position

What is claimed is:

1. An endoscope comprising:

a bending operating member and an elevator operation lever attached to a body part of an operating part, the elevator operation lever being operated to displace an elevation angle of a treatment tool elevator for elevating a treatment tool provided in a distal end of an insertion part, wherein the elevator operation lever includes a finger hook part inside which a rotational movement regulating member is provided, rotational movement of the elevator operation lever is regulated by bringing the rotational movement regulating member and an outer peripheral surface of the body part of the operating part into contact with each other, and the rotational movement regulating member protrudes toward the outer peripheral surface on both sides in a width direction inside the finger hook part, wherein, in a state where the bending operating member and the elevator operation lever are attached to the body part of the operating part, the finger hook part is attachable and detachable, and, by replacing with the finger hook part in which a position or a shape of the rotational movement regulating member is different, a range of rotational movement of the treatment tool elevator is changed.

2. The endoscope according to claim 1, wherein the range of rotational movement of the treatment tool elevator is changed in accordance with a range of the rotational movement of the elevator operation lever.

3. The endoscope according to claim 1, wherein, by changing the position or the shape of the rotational movement regulating member, the range of rotational movement of the treatment tool elevator is changed.

4. The endoscope according to claim 1, wherein, by changing a height in a direction perpendicular to an installation surface or a width in a direction horizontal to the installation surface of the rotational movement regulating member, the range of rotational movement of the treatment tool elevator is changed.

5. The endoscope according to claim 1, wherein the endoscope includes a plurality of elevator operation levers having different positions or shapes of the rotational movement regulating members, and the range of rotational movement of the treatment tool elevator is changed as the elevator operation lever is replaced.

* * * * *